(12) United States Patent
Bukesov et al.

(10) Patent No.: US 12,150,623 B2
(45) Date of Patent: Nov. 26, 2024

(54) TECHNIQUES FOR COMPOSITION IDENTIFICATION OF AN ANATOMICAL TARGET

(71) Applicant: GYRUS ACMI, INC., Westborough, MA (US)

(72) Inventors: Sergey A. Bukesov, Acton, MA (US); Kurt G. Shelton, Bedford, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

(21) Appl. No.: 17/393,878

(22) Filed: Aug. 4, 2021

(65) Prior Publication Data
US 2022/0039641 A1 Feb. 10, 2022

Related U.S. Application Data

(60) Provisional application No. 63/061,256, filed on Aug. 5, 2020.

(51) Int. Cl.
*A61B 1/06* (2006.01)
*A61B 1/00* (2006.01)
*A61B 1/05* (2006.01)

(52) U.S. Cl.
CPC ........ *A61B 1/0638* (2013.01); *A61B 1/00009* (2013.01); *A61B 1/05* (2013.01); *A61B 1/0684* (2013.01)

(58) Field of Classification Search
CPC ............ A61B 1/00009; A61B 1/00096; A61B 1/00165; A61B 1/0638; A61B 1/0669; A61B 1/05; A61B 1/07
See application file for complete search history.

(56) References Cited

U.S. PATENT DOCUMENTS 4,957,114 A * 9/1990 Zeng .................... A61B 5/0059
600/476
5,557,324 A 9/1996 Wolff
(Continued)

FOREIGN PATENT DOCUMENTS

| CN | 116075849 A | 5/2023 |
|---|---|---|
| DE | 112021004135 T5 | 5/2023 |

(Continued)

OTHER PUBLICATIONS

"International Application Serial No. PCT/US2021/044501, International Search Report mailed Nov. 12, 2021", 6 pgs.
(Continued)

*Primary Examiner* — John P Leubecker
*Assistant Examiner* — Jae Woo
(74) *Attorney, Agent, or Firm* — Schwegman Lundberg & Woessner. P.A.

(57) ABSTRACT

Techniques for identifying composition of an anatomical target using a series of different colored light sources are provided. In an example, a method can include emitting light from multiple illumination sources, receiving an illumination response from an anatomical target at an optical sensor, providing an image representative of the anatomical target, and providing spectral intensity information of the illumination response in addition to the image. Each illumination source can emit light having a range of frequencies centered about a different frequency than each other illumination source.

20 Claims, 6 Drawing Sheets

(56) References Cited

U.S. PATENT DOCUMENTS

| | | | |
|---|---|---|---|
| 6,537,211 B1* | 3/2003 | Wang | G01J 3/02 |
| | | | 600/178 |
| 6,554,824 B2 | 4/2003 | Davenport et al. | |
| 7,442,167 B2 | 10/2008 | Dunki-jacobs et al. | |
| 8,616,747 B2 | 12/2013 | Yabe | |
| 9,017,316 B2 | 4/2015 | Khatchaturov et al. | |
| 9,445,871 B2 | 9/2016 | Kang et al. | |
| 9,486,286 B2 | 11/2016 | Hodel et al. | |
| 9,757,199 B2 | 9/2017 | Chia et al. | |
| 9,949,615 B2 | 4/2018 | Zappia et al. | |
| 9,968,403 B2 | 5/2018 | Hasenberg et al. | |
| 10,039,604 B2 | 8/2018 | Chia et al. | |
| 10,067,304 B2 | 9/2018 | Yu et al. | |
| 10,105,184 B2 | 10/2018 | Beck et al. | |
| 10,175,435 B2 | 1/2019 | Peng et al. | |
| 10,258,415 B2 | 4/2019 | Harrah et al. | |
| 10,383,690 B2 | 8/2019 | Hodel et al. | |
| 2003/0050532 A1 | 3/2003 | Doguchi | |
| 2004/0044287 A1* | 3/2004 | Lin | G01N 21/6486 |
| | | | 600/475 |
| 2009/0306478 A1* | 12/2009 | Mizuyoshi | A61B 1/0655 |
| | | | 600/178 |
| 2012/0130166 A1 | 5/2012 | Nishimura et al. | |
| 2014/0160318 A1* | 6/2014 | Blanquart | H04N 23/12 |
| | | | 348/234 |
| 2015/0224249 A1 | 8/2015 | Ciulla et al. | |
| 2015/0230864 A1 | 8/2015 | Xuan et al. | |
| 2015/0272674 A1 | 10/2015 | Xuan et al. | |
| 2016/0081749 A1 | 3/2016 | Zhang et al. | |
| 2016/0166319 A1 | 6/2016 | Yu et al. | |
| 2017/0245745 A1 | 8/2017 | Ohara | |
| 2017/0328540 A1* | 11/2017 | Paul | G03B 21/204 |
| 2018/0092693 A1 | 4/2018 | Falkenstein et al. | |
| 2019/0113700 A1 | 4/2019 | Peng et al. | |
| 2019/0151022 A1 | 5/2019 | Yu et al. | |
| 2019/0159839 A1 | 5/2019 | Zhang et al. | |
| 2019/0192237 A1 | 6/2019 | Harrah et al. | |
| 2019/0201038 A1* | 7/2019 | Yates | A61B 18/12 |
| 2019/0246908 A1 | 8/2019 | Pyun et al. | |
| 2019/0298449 A1 | 10/2019 | Khachaturov et al. | |
| 2019/0393669 A1 | 12/2019 | Yu et al. | |
| 2020/0015668 A1* | 1/2020 | Scheib | A61B 5/1072 |
| 2020/0054280 A1* | 2/2020 | Cohen | A61B 1/000094 |
| 2020/0178781 A1* | 6/2020 | Tabata | A61B 1/00009 |
| 2020/0305259 A1* | 9/2020 | Kojima | A61B 1/07 |
| 2020/0404129 A1* | 12/2020 | Talbert | A61B 5/489 |
| 2021/0059503 A1 | 3/2021 | Tanaka et al. | |
| 2021/0321866 A1* | 10/2021 | Schuster | A61B 1/046 |

FOREIGN PATENT DOCUMENTS

| | | |
|---|---|---|
| EP | 2130484 | 12/2009 |
| EP | 3510962 | 7/2019 |
| EP | 3512448 | 7/2019 |
| EP | 3522811 | 8/2019 |
| JP | 2002102142 A | 4/2002 |
| JP | 2009297290 A | 12/2009 |
| JP | 2017525304 A | 8/2017 |
| WO | 1990014797 | 12/1990 |
| WO | 2015178879 | 11/2015 |
| WO | WO-2015185661 A1 | 12/2015 |
| WO | WO-2019225074 A1 | 11/2019 |
| WO | 2020033121 | 2/2020 |
| WO | WO-2022031817 A1 | 2/2022 |

OTHER PUBLICATIONS

"International Application Serial No. PCT/US2021/044501, Written Opinion mailed Nov. 12, 2021", 5 pgs.

"International Application Serial No. PCT/US2021/044501, International Preliminary Report on Patentability mailed Feb. 16, 2023", 7 pgs.

"Japanese Application Serial No. 2023-507795, Notification of Reasons for Refusal mailed Dec. 18, 2023", w/ English Translation, 26 pgs.

"Japanese Application Serial No. 2023-507795, Response filed Mar. 26, 2024 to Notification of Reasons for Refusal mailed Dec. 18, 2023", w/ english claims, 10 pgs.

"Indian Application Serial No. 202347003134, First Examination Report mailed Apr. 29, 2024", 6 pgs.

"Japanese Application Serial No. 2023-507795, Decision of Rejection mailed Jul. 1, 2024", with English translation, 21 pgs.

* cited by examiner

TECHNIQUES FOR COMPOSITION IDENTIFICATION OF AN ANATOMICAL TARGET

CROSS-REFERENCE TO RELATED APPLICATION

This application claims the benefit of priority to U.S. Provisional Patent Application Ser. No. 63/061,256, filed Aug. 5, 2020, the contents of which are incorporated herein by reference in their entirety.

FIELD OF THE DISCLOSURE

The present invention relates to target identification and, more particularly to techniques for identifying composition of an anatomical target using a series of different colored light sources.

BACKGROUND OF THE DISCLOSURE

Medical scopes allow a user to inspect hidden areas of a patient. Scopes for visual inspection of certain internal areas of a patient, such as endoscopes and laparoscopes, were first developed in the early 1800s and have been used to inspect inside the body. A typical medical scope consists of a distal end comprising an optical or electronic imaging system and a proximal end with controls for manipulating the tools and devices for viewing the image, with a solid or tubular elongate shaft connecting the ends. Some medical scopes allow a physician to pass tools or treatments down a hollow channel, for example, to resect tissue or retrieve objects.

Efficient use of a medical scope depends on several factors such as experience, dexterity, and visual cues. Medical scopes that allow for interaction within small confined space of a patient's body often use a screen or monitor to project an image of the area about the distal end of the medical scope. Improvement of the displayed images can allow for more efficient use of the medical scope.

SUMMARY OF THE DISCLOSURE

Techniques for identifying composition of an anatomical target using a series of different colored light sources are provided. In an example, a method can include emitting light from multiple illumination sources, receiving an illumination response from an anatomical target at an optical sensor, providing an image representative of the anatomical target, and providing spectral intensity information of the illumination response in addition to the image. Each illumination source can emit light having a range of frequencies centered about a different frequency than each other illumination source.

This section is intended to provide an overview of subject matter of the present patent application. It is not intended to provide an exclusive or exhaustive explanation of the invention. The detailed description is included to provide further information about the present patent application.

DETAILED DESCRIPTION

A medical scope can provide a view of an anatomical target of a patient. Such medical scopes can include but are not limited to, an endoscope, laparoscope, or variations, and other types of scopes used for diagnostic and therapeutic procedures. During a medical scope procedure, a physician can control the position of the end of the scope to view an anatomical target. Whether diagnostic or therapeutic, composition of the anatomical target can provide additional information that can benefit efficiency and efficacy of many procedures. The present inventors have discovered techniques to supplement imaging of medical scope procedures. Such supplementation can include providing composition information about an anatomical target as the target is conventionally observed with the medical scope.

Figure 1:
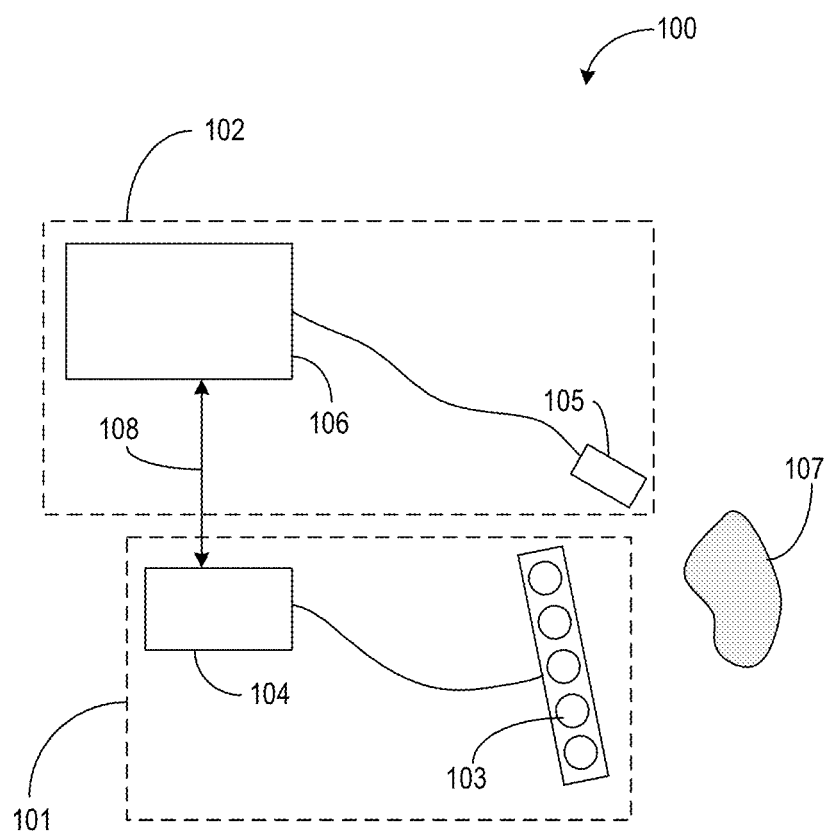
FIG. 1 illustrates generally a composition identification system 100 according to the present subject matter.

FIG. 1 illustrates generally a composition identification system 100 according to the present subject matter. The composition identification system 100 can include a lighting system 101 and an imaging system 102. The lighting system 101 can include multiple illumination sources 103 and a controller 104. The imaging system can include an optical sensor 105 and a controller 106. Each illumination source 103 can provide light having a narrow range of wavelengths. The narrow range of wavelengths of each illumination source 103 can surround a center frequency characteristic of the color of the light emitted by the illumination source 103, and the center frequency of a first illumination source 103 can be different than the center frequency of the other illumination sources. It is understood that an illumination source may include more than one light source capable of providing the narrow range of wavelengths characteristic of the illumination source. For example, if an illumination source provides "blue" light from light-emitting diodes (LEDs), the illumination source may have several "blue" LEDs. A beneficial aspect of the lighting system 101 is that the illumination sources 103 of the lighting system 101 can be activated by the controller 104 in a sequential pattern such that the light emitted from the lighting system 101 appears, to some systems as well as to users of the composition identification system 100, to be white light. In some examples, in addition to providing on/off control of each illumination source, the controller 104 can modulate other aspects of each individual illumination source such as amplitude, on/off duty cycle, intensity, or combinations thereof. While the illumination sources 103 are sequentially illuminating an anatomical target 107, a second controller, such as the controller 106 of the imaging system 102, can acquire a spectral profile of light reflected from the target 105 to determine or estimate a composition of the target 105. Because the emitted light of the lighting system 101 can appear as white light or light having a broad range of the visible light spectrum, the lighting system 101 can be used to provide illumination for visually identifying anatomical targets 107 as well as for electronically observing and recording images of the anatomical target 107. At the same time, the spectral profile can be very accurate because the illumination light used to form the profile are of a predetermined wavelength and intensity and images catching response illumination of an individual illumination source can be captured and evaluated. The colors chosen for the individual illumination sources 103 can be associated with spectral profiles of known compositions.

In certain examples, a controller 104, 106 can compile a spectral profile of response illumination captured at the optical sensor 105. The spectral profile can reveal levels of how the colors of the illumination sources 103 are or are not absorbed by the anatomical target 107. If the spectral profile matches a known profile, the composition of the anatomical target 107 can be determined. Although such analysis can be done using white light having a broad spectrum of random wavelengths and intensities, using the predetermined narrow band wavelength illumination sources 103 of the example lighting system 101 can allow for less noise compared to the random wavelengths of the conventional system and faster acquisition of the spectral profile of the response illumination because of the predetermined narrow band of each of the illumination wavelengths as well as the predetermined intensity of each illumination source 103.

In certain examples, a controller 106 of the imaging system 102 and a controller 104 of the lighting system 101 can be coupled via a communication link 108 to synchronize sequencing of the multiple illumination sources 103 and the sampling of the optical sensor 105. In certain examples, the multiple illumination sources 103 can include an LED, a laser, a quantum dot, or combinations thereof.

Figure 2A:
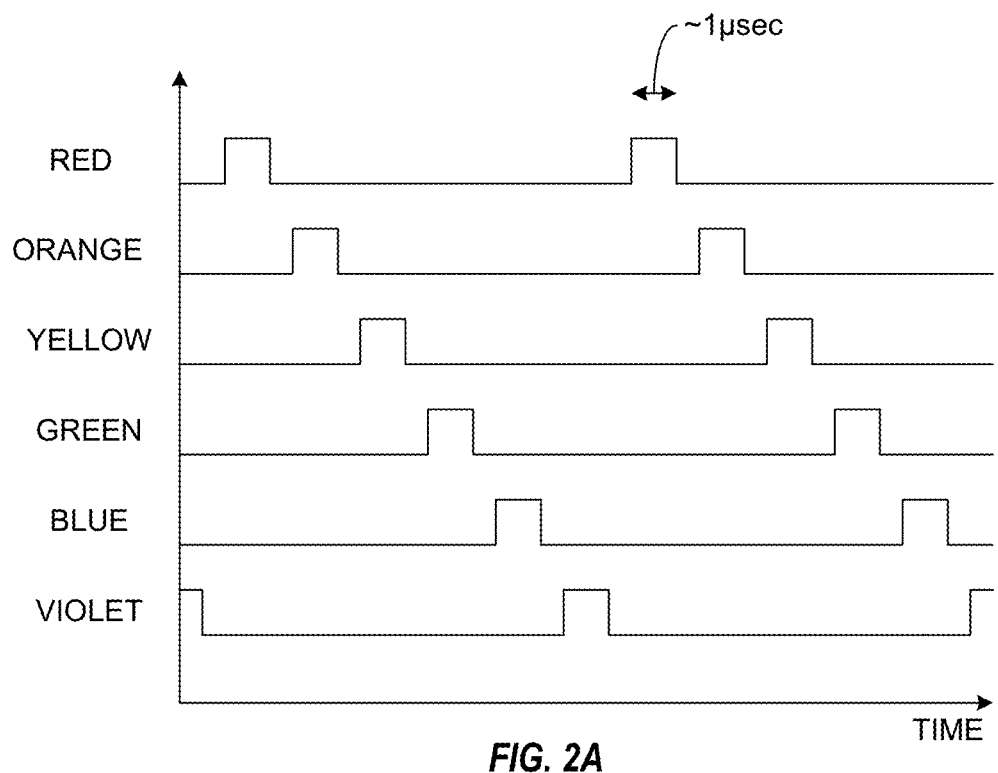
FIG. 2A illustrates graphically a method of operating an example lighting system according to the present subject matter.

FIG. 2A illustrates graphically a method of operating an example lighting system (e.g., FIG. 1, 101) according to the present subject matter. The lighting system can include multiple illumination sources. Each illumination source can project light having wavelength different than several other illumination sources of the lighting system. For example, a first illumination source can project light having a wavelength of about 400 nanometers (nm), a second illuminations source can project light having a wavelength of around 500 nm, and a third illumination source can project light having a wavelength of around 630 nm. In some examples, the lighting system can have additional illumination sources capable of projecting light having a unique wavelength or unique center frequency. In the plot of the example of FIG. 2A, the lighting system includes illumination sources capable of individually generating red, orange yellow, green, blue and violet light. The plot of the control signals of the illumination sources of the lighting system indicates that the method can pulse each illumination source on at any one time for a small interval, for example, on the order of a microsecond His) or so. The method indicates that the lighting system continually provides illumination. In certain examples, an illumination period of one illumination source can overlay with a portion of an illumination period of a second illumination source. In some examples, the composite illumination provided by the sequential pulsing of the multiple illumination sources of the example lighting system can appear as white light or light having a full spectrum of visible frequencies such that cycling of the individual illumination sources is not detectable to the human eye. As such, an optical sensor, camera, or display of an imaging system can capture and project well-lit images of a viewing area and display the image. For applications that do not require a clear and well-lit image, the interval that an individual illumination source is activated can be longer than 1 µs such as on the order of several milliseconds (ms) or longer.

Figure 2B:
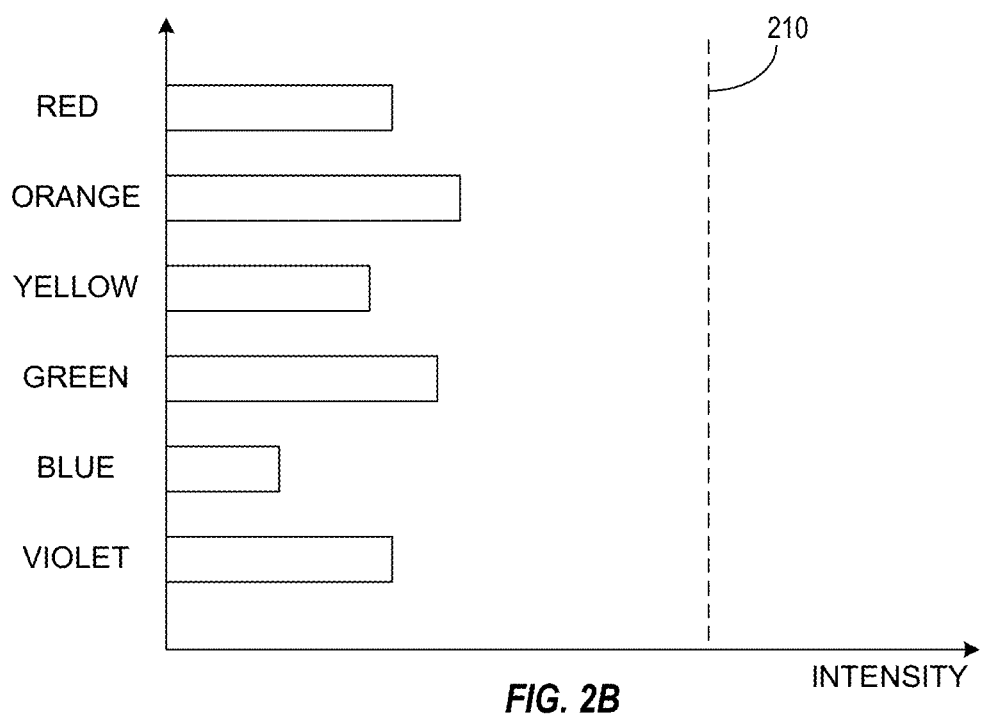
FIG. 2B illustrates an example spectral profile provided by an example controller.

As the target is illuminated, an optical sensor can collect response illumination by a single illumination source of the lighting system and a controller can analyze the image to assess an absorption rate by the target of the specific color projected by the illumination source. As the lighting system repeatedly enables and disables each illumination source, the controller can integrate the absorption information for each wavelength projected at the target by the illumination sources of the lighting system and can compile a spectral profile of the target. In certain examples, the controller capturing the images for spectral analysis can be synchronized with the controller of the lighting system. FIG. 2B illustrates an example spectral profile provided by an example controller. The example spectral profile includes a line 210 marking an expected normalized intensity for response illumination from a white reference target. The spectral profile information can provide an indication of the composition of the target. In some examples, the spectral profile information can be displayed with the image captured by the camera and a user can get timely feedback that allows for a determination of a composition of the target. Such feedback can be instructive to the operator about how to plan or adjust treatment of the target depending on whether the system is used diagnostically or commensurate with applying therapy.

In certain examples, a controller can control the sequencing of the illumination sources while synchronizing the capture of images when a particular illumination source is illuminating the target. For example, the controller can initiate the illumination interval of a first illumination source. When the first illumination source is providing illumination of the target, the controller can provide a signal to the imaging system to capture a single image of the target illuminated with only the light of the first illumination source.

Figure 3:
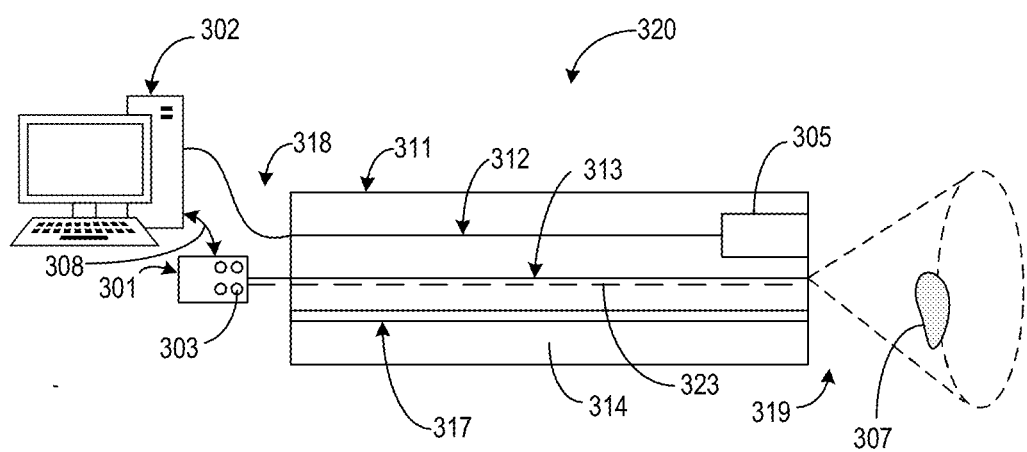
FIG. 3 illustrates generally a system employing an example composition identification system according to the present subject matter.

FIG. 3 illustrates generally a system 320 employing an example composition identification system according to the present subject matter. The system 300 can include a medical scope 311, a lighting system 301, and an imaging system 302. In some examples, the imaging system 302 can include a monitor, coupled to a proximal end 318 of the medical scope 311, to display an image of an anatomical target 307 at a distal end 319 of the medical scope 311. The medical scope 311 can include a shaft 314, or probe, an optical sensor 306 and an illumination path or optical path 313. The shaft 314 can be extended into an orifice or incision of a patient. In some examples, the shaft 314 can be flexible to navigate twist and turns while being positioned to the anatomical target 307. The shaft 314 can include one or more channels 317.

The optical sensor 306 can integrated with the shaft. The optical sensor 306 can receive light from the area about the distal end 319 of the shaft including light reflected or generated by an anatomical target 307. The optical sensor 306 can provide an image signal 312 to the imaging system 302. In certain examples, the imaging system 302 can include a display or monitor such that a user of the medical scope 311 can see real-time images of an anatomical target 307.

The lighting system can illuminate the anatomical target 307 so that the optical sensor 306 can capture an image or other optical effects of the anatomical target 307. In certain examples, the lighting system can be part of the medical scope 311. In some examples, the lighting system can be separate from the medical scope 311. In certain examples, light from multiple illumination sources 303 of the lighting system can be conveyed via an optical path 313 of the shaft of the medical scope. In certain examples, the lighting system can include multiple illumination sources 303. Each illumination source 303 can provide light of a color different than the other illumination sources. For example, a first illumination source can provide light having a narrow frequency range centered about a first frequency, and each other illumination source of the lighting system can provide light having a narrow frequency range center about other frequencies. In certain examples, each illumination source can emit light centered about a frequency or wavelength different from the light emitted from each other illumination source. In some examples, the bound frequency of light of each illumination source is visible light but the present subject matter is not so limited. Full-width at half-maximum (FWHM) is a parameter commonly used to describe the width of a "bump" on a curve or function. It is given by the distance between points on the curve at which the function reaches half its maximum value. In certain examples, each illumination source can provide light having a FWHM of less 20 nanometers (nm). In some examples, the FWHM parameter for one or more of the illumination sources can be less than 10 nm. In some examples, the FWHM parameter for one or more of the illumination sources can be less than 5 nm.

Figure 6:
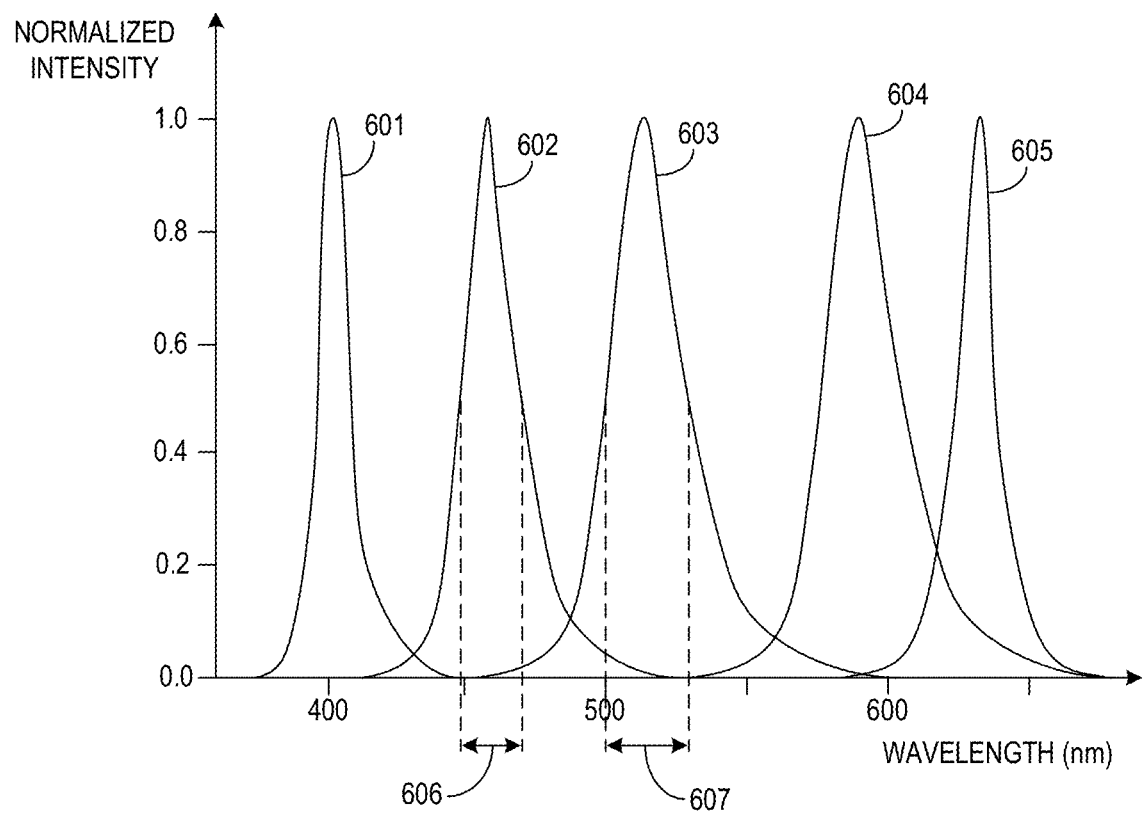
FIG. 6 illustrates generally wavelength plots of several illumination sources, normalized by intensity, that may be used in an example system of the present subject matter.

FIG. 6 illustrates generally wavelength plots of several illumination sources, normalized by intensity, that may be used in an example system of the present subject matter. The plots include a first wavelength plot 601 for violet light source where the wavelengths of the violet illumination source is centered at about wavelength of about 401 nm. The plot includes a second wavelength plot 602 for blue light source where the wavelengths of the blue illumination source is centered at about wavelength of about 456 nm. The plot includes a third wavelength plot 603 for green light source where the wavelengths of the green illumination source is centered at about wavelength of about 511 nm. The plot includes a fourth wavelength plot 604 for orange light source where the wavelengths of the orange illumination source is centered at about wavelength of about 588 nm. The plot includes a fifth wavelength plot 605 for red light source where the wavelengths of the red illumination source is centered at about wavelength of about 634 nm. Also illustrated in FIG. 6 is a measure of full-width at half-maximum (FWHM) 606, 607 for the second and third wavelength plots 602, 603. A rough estimate indicates that the FWHM 606 for the second wavelength plot is about 35 nm and the FWHM 607 for the third wavelength plot is about 25 nm.

Referring again to FIG. 3, in certain examples, the multiple illumination sources 303 can assist in determining the composition of the anatomical target 307. For example, the illustrated system may be used to diagnose or rectify certain conditions where a "stone", such as a kidney stone, is causing a health issue. Knowledge of the stone composition can assist in selecting a proper therapy to correct the health issue. Determination of the stone composition can include illuminating the stone with different colors or frequencies of electromagnetic radiation emitted from the multiple illumination sources 303, capturing the reflected or florescence of the applied illumination with the optical sensor 306, and analyzing the captured light and a level of absorption of the illumination light to determine the composition of the anatomical target 307. It is understood that light of the visible colors are a form of electromagnetic radiation. In certain examples, a controller of the imaging system 302 and a controller of the lighting system 301 can be coupled via a communication link 308 to synchronize sequencing of the multiple illumination sources 403 and the sampling of the optical sensor 305. In certain examples, the multiple illumination sources 303 can include an LED, a laser, a quantum dot, or combinations thereof.

In certain examples, the optical path 313 can include one or more optical fibers for transmitting light from the multiple illumination sources 303. In certain examples, the shaft 314 can include one or more optional optical paths 323. In certain examples, the combined light from the multiple illumination sources 303 can be transmitted via a common optical media such as a common optical fiber or optical fiber cable. In some examples, the light from the multiple illumination sources 303 can be separately transmitted via multiple optical paths or multiple optical media such as multiple optical fibers or multiple optical fiber cables. In some examples, light from each illumination source 303 can be individually transmitted via an individual optical media from the proximal end of the shaft 314 to the distal end of the shaft 314. In some examples, light from a subset of illumination sources of the multiple illumination sources 303 can be transmitted as an individual group via an individual optical media from the proximal end of the shaft 314 to the distal end of the shaft 314.

Figure 4:
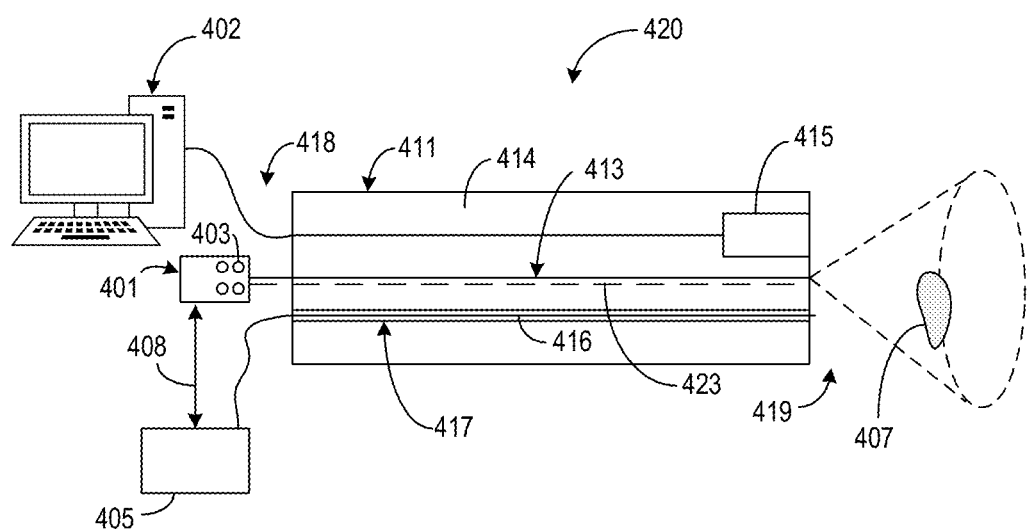
FIG. 4 illustrates generally a system employing an example composition identification system according to the present subject matter.

FIG. 4 illustrates generally a system employing an example composition identification system 400 according to the present subject matter. The system 400 can include a medical scope 411 and an imaging system 420. In some examples, the imaging system 420 can include camera 415 at a distal end 419 of the medical scope 411, and a monitor 402, coupled to a proximal end 418 of the medical scope 411, to display an image of an anatomical target 407 located at the distal end 419 of the medical scope 411. In some examples, the medical scope 411 can include a shaft 414, or probe, the camera 415 and a lighting system. The shaft 414 can be extended into an orifice or incision of a patient. In some examples, the shaft 414 can be flexible to navigate twist and turns while being positioned to the anatomical target. The shaft can include one or more channels 417.

The camera 415 can be located in one of the channels of the shaft 414. The camera 415 can receive light from the area about the distal end 419 of the shaft 414 including light reflected or generated by an anatomical target 407. The camera 415 can provide an image signal to the imaging system 420. In certain examples, the monitor 402 of the imaging system 420 can display images such that a user of the medical scope 411 can see real-time images of the anatomical target 407.

The lighting system 401 can illuminate the anatomical target 407 so that the camera 415 can capture an image or other optical effects of the anatomical target 407. In certain examples, the lighting system 401 can be part of the medical scope 411. In some examples, the lighting system 401 can be separate from the medical scope 411. In certain examples, light from an illumination source of the lighting system 401 can be conveyed via an optical path 413 of the shaft 414, or one or more optional optical paths 423, of the medical scope 411. In certain examples, the lighting system 401 can include multiple illumination sources 403. Each illumination source 403 can provide light of a color different than the other illumination sources. For example, a first illumination source can provide light having a narrow frequency range centered about a first frequency, and each other illumination source of the lighting system can provide light having a narrow frequency range center about other frequencies. In some examples, the bound frequency of light of each illumination source is visible light but the present subject matter is not so limited.

In certain examples, the multiple illumination sources 403 can assist in determining the composition of the anatomical target 407. For example, the illustrated system 400 may be used to diagnose or rectify certain conditions where a "stone", such as a kidney stone, is causing a health issue. Knowledge of the stone composition can assist in selecting a proper therapy to correct the health issue. Determination of the stone composition can include illuminating the stone with different colors or frequencies of electromagnetic radiation, capturing reflected illumination or florescence of the applied illumination with the optical sensor 405, and analyzing the captured light and a level of absorption of the illumination light to determine the composition of the anatomical target 407.

In certain examples, the optical sensor 405 can receive response illumination, such as light from the lighting system that reflects from the anatomical target 407 and areas about the anatomical target 407. The optical sensor 405 can be located at the proximal end 418 of the shaft 414 and can receive the response illumination via an optical path 416 extending within the working channel 417 of the medical scope 411. In certain examples, the optical path 416 can include an optical fiber or an optical cable. In certain examples, a controller of the optical sensor 405 and a controller of the lighting system 401 can be coupled via a communication link 408 to synchronize sequencing of the multiple illumination sources 403 and the sampling of the optical sensor 405. In certain examples, the multiple illumination sources 403 can include an LED, a laser, a quantum dot, or combinations thereof.

Figure 5:
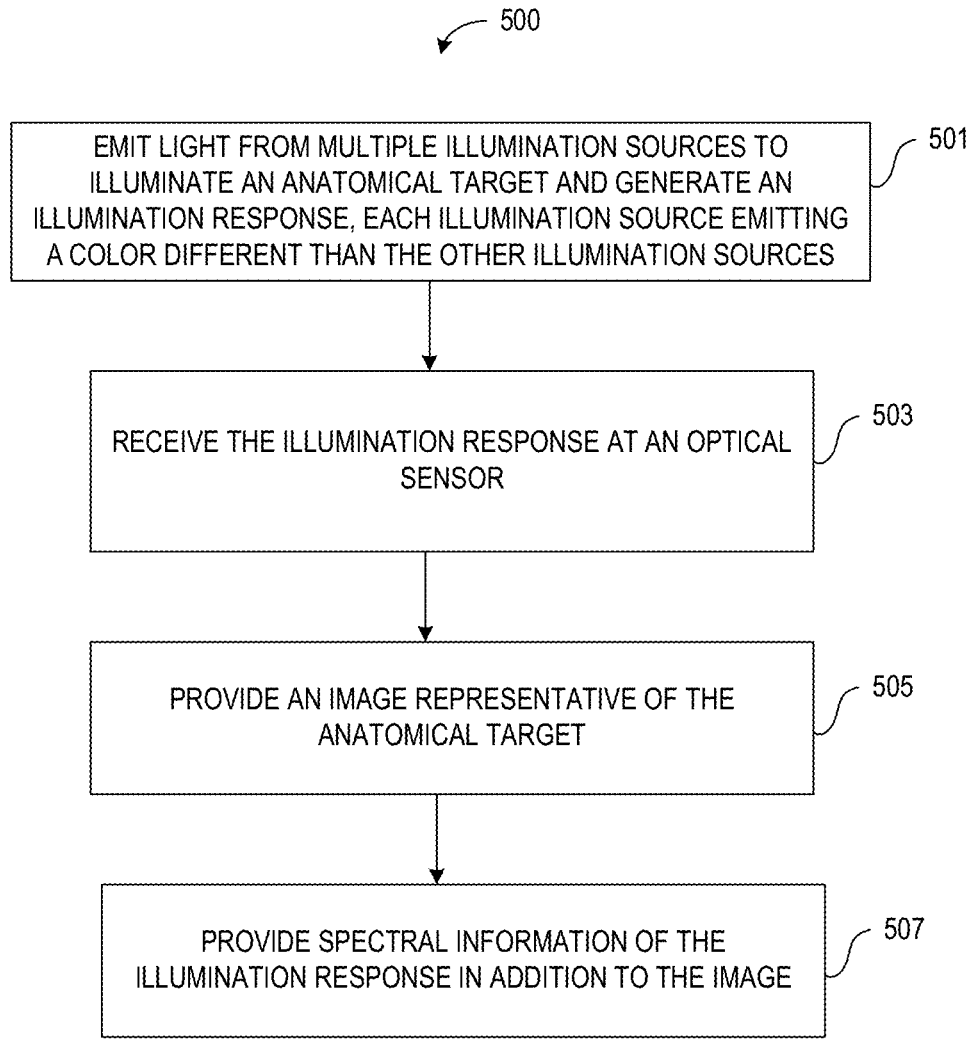
FIG. 5 illustrates generally an example method of operating a lightings system employing multiple illumination sources for determining anatomical target composition.

FIG. 5 illustrates generally an example method 500 of operating a lighting system employing multiple illumination sources for determining anatomical target composition. At 501, light from multiple illumination sources can be emitted from a lighting system to illuminate an anatomical target and to generate an illumination response. In some examples, each individual illumination source can emit light having a color different from the other illumination sources. In certain examples, the illumination sources can be pulsed in a serial fashion such that only a portion of the multiple illumination sources emit light any particular instant. In some examples, the serial pulsing of the illumination sources can allow for each color of the illumination sources to be the only color emitted at a particular instant. At the same time, the effect of the serial pulsing of the illumination sources can appear as though the lighting system is emitting white light or light having a wide range of wavelengths across the visible light spectrum.

At 503, an optical sensor can receive the illumination response from the anatomical target. In certain examples, the optical sensor can include a light-sensitive transistor such as a CMOS device or can include light sensitive charged-coupled devices (CCDs). In some examples, the optical sensor can be a spectrometer. At 505, an image of the anatomical target can be provided for example, via a monitor, to the user. At 507, spectral information can be provided about the anatomical target to the user. The spectral information can be derived from the illumination response received at the optical sensor. In some examples, the spectral information can be provided via a second monitor. In some examples, the spectral information can be provided via the same monitor providing the image. In certain examples, a controller can compare the spectral information that may be in the form of a spectral profile to known profiles of materials and phenomenon. As such, if the derived spectral profile matches a known material or phenomenon within a certain degree of certainty, an alarm or indication can be displayed on the monitor for the user. In certain examples, the optical sensor can include multiple light sensing devices mapped to a field of view and the spectral profile can include spectral information for multiple areas within the field of view. As such, if the derived spectral profile for a certain area matches a known material or phenomenon (e.g., cancerous tissue, a cyst, scar tissue, etc.), the area can be graphically highlighted to indicate a possible area of interest. In some examples, the parameters for matching a derived spectral profile to an alarm state may be conditioned on the hardness or softness of the material to which the spectral profile matches and an indication of material hardness can be displayed on the monitor.

NOTES AND EXAMPLES

In a first example, Example 1, a target analysis system can include a sensor configured to receive response illumination from an anatomical target; an illumination device comprising multiple illumination sources to illuminate the anatomical target, wherein each illumination source is configured to emit light having full width at half maximum centered about a different frequency than each other illumination source; and an image system configured to control each illumination source of the multiple illumination sources, to provide an image representative of the anatomical target, and to provide spectral intensity information of the received illumination in addition to the image.

In Example 2, the subject matter of Example 1 includes, wherein the image system is configured to provide a spectral intensity signal of the received illumination in addition to the image.

In Example 3, the subject matter of Examples 1-2 includes, wherein a full width at half maximum of light emitted by each illumination source does not overlap with a frequency range of full width at half maximum emitted light of each other illumination source.

In Example 4, the subject matter of Examples 1-3 includes, wherein the image system includes a controller configured to modulate an individual intensity of an illumination source of the multiple illumination sources.

In Example 5, the subject matter of Examples 1–4 includes, wherein the controller is configured to periodically change an intensity state of the illumination device to provide a time-wise chain of multiple illumination states; wherein a first illumination state of the multiple illumination states is different than a second, immediately prior, illumination state of the multiple illumination states; and wherein the first illumination state is different than a third, immediately subsequent, illumination state of the multiple illumination states.

In Example 6, the subject matter of Example 5 includes, microsecond.

In Example 7, the subject matter of Examples 1-6 includes, an endoscope configured to support the sensor.

In Example 8, the subject matter of Example 7 includes, a first optical path configured to conduct the response illumination from a first end of the endoscope to a second end of the endoscope.

In Example 9, the subject matter of Example 8 includes, an optical sensor configured to receive the illumination response from the first optical path.

In Example 10, the subject matter of Example 9 includes, wherein the optical sensor includes a camera.

In Example 11, the subject matter of Examples 9-10 includes, wherein the optical sensor includes a spectrometer.

In Example 12, the subject matter of Examples 1-11 includes, wherein the multiple illumination sources include more than two illumination sources.

In Example 13, the subject matter of Examples 1-12 includes, wherein the multiple illumination sources include a quantum dot.

Example 14 is a method of identifying a composition of an anatomical, the method comprising emitting light from multiple illumination sources to illuminate an anatomical target and to generate an illumination response, each illumination source is configured to emit light having a range of frequencies centered about a different frequency than each other illumination source; receiving the illumination response from an anatomical target at an optical sensor; providing an image representative of the anatomical target; and providing spectral intensity information of the illumination response in addition to the image.

In Example 15, the subject matter of Example 14 includes, wherein the emitting light from the multiple illumination sources includes temporally sequencing pulses of light from each of the multiple illumination sources to provide temporally sequenced pulses of light.

In Example 16, the subject matter of Example 15 includes, acquiring one or more images of the anatomical target during each pulse of light of the temporally sequenced pulses of light.

In Example 17, the subject matter of Example 16 includes, synchronizing the temporally sequencing pulses of light from each of the multiple illumination sources with the acquiring one or more images of the anatomical target.

In Example 18, the subject matter of Examples 15-17 includes, microseconds.

In Example 19, the subject matter of Examples 15-18 includes, microseconds.

In Example 20, the subject matter of Examples 15-19 includes, wherein the multiple illumination sources include a quantum dot.

Example 21 is at least one machine-readable medium including instructions that, when executed by processing circuitry, cause the processing circuitry to perform operations to implement of any of Examples 1-20.

Example 22 is an apparatus comprising means to implement of any of Examples 1-20.

Example 23 is a system to implement of any of Examples 1-20.

Example 24 is a method to implement of any of Examples 1-20.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, the terms "including" and "comprising" are open-ended, that is, a system, device, article, composition, formulation, or process that includes elements in addition to those listed after such a term are still deemed to fall within the scope of subject matter discussed. Moreover, such as may appear in a claim, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of a claim. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. The following aspects are hereby incorporated into the Detailed Description as examples or embodiments, with each aspect standing on its own as a separate embodiment, and it is contemplated that such embodiments can be combined with each other in various combinations or permutations.

What is claimed is:

1. A target analysis system comprising:
   an illumination device comprising multiple illumination sources configured to illuminate an anatomical target with illumination, the multiple illumination sources configured to emit light having different wavelengths and being configured to be sequentially activated to produce the illumination such that a time average of the illumination, as perceptible by a human eye, appears as white light;
   at least one optical sensor configured to receive, as response illumination, a portion of the illumination that is reflected from the anatomical target in response to the emission light from each of the illumination sources and based at least in part on the response illumination, form an image signal; and
   a controller configured to:
   provide, from the image signal, an image representative of the anatomical target;
   provide, from the response illumination, spectral intensity information of the received response illumination; and
   determine, based at least in part on the spectral intensity information, a composition of the anatomical target.

2. The target analysis system of claim 1, wherein the controller is configured to provide a spectral intensity signal of the received response illumination in addition to the image.

3. The target analysis system of claim 1, wherein the multiple illumination sources are configured to emit light having respective wavelength spectra that do not overlap with one another.

4. The target analysis system of claim 1, wherein the controller is configured to modulate an individual intensity of an illumination source of the multiple illumination sources.

5. The target analysis system of claim 4, wherein the controller is configured to periodically change an intensity state of the illumination source to provide a time-wise chain of multiple illumination states;
   wherein a first illumination state of the multiple illumination states is different than a second, immediately prior, illumination state of the multiple illumination states; and
   wherein the first illumination state is different than a third, immediately subsequent, illumination state of the multiple illumination states.

6. The target analysis system of claim 5, wherein a period of each illumination state of the time-wise chain of multiple illumination states is less than or equal to 1 microsecond.

7. The target analysis system of claim 1, further comprising an endoscope configured to support the at least one optical sensor.

8. The target analysis system of claim 7, including a first optical path configured to conduct the response illumination from a first end of the endoscope to a second end of the endoscope.

9. The target analysis system of claim 8, wherein the at least one optical sensor is configured to receive the response illumination from the first optical path.

10. The target analysis system of claim 9, wherein the at least one optical sensor includes a camera.

11. The target analysis system of claim 9, wherein the at least one optical sensor includes a spectrometer.

12. The target analysis system of claim 1, wherein the multiple illumination sources include more than two illumination sources.

13. The target analysis system of claim 1, wherein at least one illumination source of the multiple illumination sources includes a quantum dot.

14. A method of identifying a composition of an anatomical target, the method comprising:
   emitting light having different wavelengths sequentially from multiple illumination sources to provide illumination such that a time average of the illumination, as perceptible by a human eye, appears as white light;
   reflecting at least some of the illumination from the anatomical target to produce response illumination;
   receiving, with at least one optical sensor, at least some of the response illumination to form an image signal;
   providing, from the image signal, an image representative of the anatomical target;
   providing, from the response illumination, spectral intensity information of the response illumination; and
   determining, based at least in part on the spectral intensity information, the composition of the anatomical target.

15. The method of claim 14, wherein the emitting light having different wavelengths sequentially from the multiple illumination sources includes temporally sequencing pulses of light from each of the multiple illumination sources to provide temporally sequenced pulses of light.

16. The method of claim 15, further comprising acquiring one or more images of the anatomical target during each pulse of light of the temporally sequenced pulses of light.

17. The method of claim 16, further comprising synchronizing the temporally sequencing pulses of light from each of the multiple illumination sources with acquiring the one or more images of the anatomical target.

18. The method of claim 15, wherein the temporally sequenced pulses of light include pulses of light of less than 10 microseconds.

19. The method of claim 15, wherein the temporally sequenced pulses of light include pulses of light of less than 2 microseconds.

20. The method of claim 15, wherein at least one illumination source of the multiple illumination sources includes a quantum dot.

* * * * *